(12) United States Patent
Niedenthal et al.

(10) Patent No.: US 8,551,717 B2
(45) Date of Patent: Oct. 8, 2013

(54) METHOD FOR DETERMINING SUMOYLATION

(75) Inventors: Rainer Niedenthal, Hannover (DE); Astrid Jakobs, Hannover (DE); Jesko Koehnke, Oldenberg i.H. (DE)

(73) Assignee: Medizinische Hochschule Hannover, Hannover (DE)

( * ) Notice: Subject to any disclaimer, the term of this patent is extended or adjusted under 35 U.S.C. 154(b) by 460 days.

(21) Appl. No.: 13/054,658

(22) PCT Filed: Aug. 4, 2009

(86) PCT No.: PCT/EP2009/005634
§ 371 (c)(1),
(2), (4) Date: Jan. 18, 2011

(87) PCT Pub. No.: WO2010/015376
PCT Pub. Date: Feb. 11, 2010

(65) Prior Publication Data
US 2011/0124011 A1 May 26, 2011

(30) Foreign Application Priority Data

Aug. 4, 2008 (EP) .................... 08013924

(51) Int. Cl.
*G01N 31/00* (2006.01)
*G01N 33/53* (2006.01)
(52) U.S. Cl.
USPC ........... 435/7.21; 435/7.1; 436/501; 436/518; 422/430; 424/9.1

(58) Field of Classification Search
None
See application file for complete search history.

(56) References Cited

U.S. PATENT DOCUMENTS
2002/0031818 A1    3/2002    Ronai et al.

FOREIGN PATENT DOCUMENTS
WO    WO 2007051207    5/2007

OTHER PUBLICATIONS

Jakobs, A., "Ubc9 fusion-directed SUMOylation (UFDS): a method to analyze function of protein SUMOylation.", Nature-Methods. vol. 4, No. 3, Mar. 2007, pp. 245-250.
R. Niedenthal; "Ubc9 fusion-directed SUMOylation (UFDS)"; Biochemical Society Transactions; vol. 35, No. Pt. 6, Dec. 2007; pp. 1430-1432.
A. Jakobs et al.; "Ubc9 fusion-directed SUMOylation identifies constitutive and inducible SUMOylation"; Nucleic Acids Research, vol. 35, No. 17, 2007, p. E109.
Thakar Ketan et al.; "Sumo ylation of the hepatoma-derived growth factor negatively influences its binding to chromatin"; The FEBS Journal, vol. 275, No. 7, Apr. 2008, pp. 1411-1426.

*Primary Examiner* — Lisa Cook
(74) *Attorney, Agent, or Firm* — Whitham Curtis Christofferson & Cook, PC

(57) ABSTRACT

The present invention relates to a method for determining SUMOylation and utilizing said SUMOylation patterns for identifying specific interaction between different binding partners. In another aspect, the present invention relates to systems allowing the determination of SUMOylation and for determining specific interaction between binding partners. Furthermore, the present invention relates to vectors and proteins relating to SUMOylation.

19 Claims, 7 Drawing Sheets

METHOD FOR DETERMINING SUMOYLATION

The present invention relates to a method for determining SUMOylation and utilizing said SUMOylation patterns for identifying specific interaction between different binding partners and the building of multiprotein complexes. In another aspect, the present invention relates to systems allowing the determination of SUMOylation and for determining specific interaction between binding partners. Furthermore, the present invention relates to vectors and proteins relating to SUMOylation.

PRIOR ART

Functions of proteins are often controlled by post-translational modifications such as phosphorylation, myristoylation, acetylation, ubiquitination and SUMOylation. These modifications can be constitutively or regulated and often prime or hinder further modifications. Protein SUMOylation is a reversible conjugation process with strong similarity to ubiquitination where the SUMO (small ubiquitin like modifier) protein is attached in a process of three enzymatic steps via an isopeptide bond to the ε-amino group of a lysine residue of the substrate. In a fourth step conjugated SUMO can be released by SUMO specific proteases (Geiss-Friedlander and Melchior, Nat Rev Mol Cell Biol, 2007, 947-956). FIG. 1 provides an overview of the SUMO pathways.

In short, C-terminal specific hydrolase-catalyzed removal of the C-terminal tail from SUMO precursor renders the SUMO precursor into the mature SUMO protein available for E1 (activating enzyme)-catalyzed SUMO activation, E2 (conjugating enzyme)-catalyzed SUMO conjugation and E3 (ligating enzyme)-mediated SUMO litigation to the substrate. DeSUMOylation counterbalances SUMOylation by freeing substrates from SUMO binding. E1 and E3 may be present in either a heterodimeric form or in different forms of peptides (E3), E2 is known as a single component only, namely the product (Ubc9 (SUMO-conjugating enzyme UBC9)) of the UBE2I (gene name for the Ubiquitin-conjugating enzyme E2 I) gene. In addition, SUMO itself exists in various forms.

SUMOylation is involved in the regulation of several proteins and, consequently, potentially interferes with other regulatory protein modifications. For example, some transcription factors, such as HSF1 (Heat shock factor protein 1), GATA-1 (Erythroid transcription factor) and MEF2A (Myocyte-specific enhancer factor 2A) are regulated by phosphorylation-dependent SUMOylation (Hietakangas et al., Mol Cell Biol., 2003, 2953-2968; Gre'goire et al., J Biol Chem., 2006, 4423-4433; Hietakangas et al., Proc Natl Acad Sci USA, 2006, 45-50) while for transcription factors MEF2D (Myocyte-specific enhancer factor 2D), HIC1 (Hypermethylated in cancer 1 protein), NF-IL-6 (C/EBP-related transcription factor) and SP-3 (GC box binding transcription factor) interplay between SUMOylation and acetylation is described (e. g. Gre'goire and Yang, Mol Cell Biol., 2005, 2273-2287). In addition, ubiquitination competes sometimes with SUMOylation (Desterro et al., Mol Cell., 1998, 233-239) and, in addition, as recently demonstrated using an Ubc9 fusion-directed SUMOylation system, SUMOylation inhibits phosphorylation of the Y701 (tyrosin 701) site of the STAT1 (Signal transducer and activator of transcription 1) protein (Jakobs et al., Nat Methods, 2007, 245-250).

Identification and examination of the function of SUMOylation of a target protein, is often difficult and hampered by the low level of the specific modifications in the cell and by lacking possibilities to manipulate a specific protein modification independently of other modifications. Thus, an in-vivo analysis is difficult. Recently, Jakobs et al., supra and Jakobs et al., 2007, Nucleic acid research, 35 (17), 109, describe a system allowing analysis of SUMOylation using an Ubc9 (E2) fusion-directed SUMOylation system (UFDS). Therein, the Ubc9 molecule, the sole molecule enabling conjugation of the c-amino group of lysine with the C-terminal carboxyl group of the C-terminal diglycine present in mature SUMO proteins, was covalently fused with a substrate protein to be analyzed for SUMOylation. Expression of the SUMO-conjugating enzyme Ubc9 fused to the substrate protein enables direct SUMOylation of said substrate protein. For example, for the STAT1 molecule or the p53 (Cellular tumor antigen p53) molecule SUMOylation was shown (Jakobs et al., supra).

However, because of the static fusion of Ubc9 to the substrate protein of interest, the above mentioned method is not suited to study the kinetics of SUMOylation or the sequential SUMOylation after different preceding modification events.

Specific interactions, including binding, of different molecules, in particular of different proteins in a cell, are essential steps in cellular processes. The analysis of these binding properties or interactions with said binding partners provides new insights into cellular processes and allows developing new pharmaceuticals. The interaction between different molecules may be due to various types of interactions including covalent linkage between the binding partners or non-covalent linkage for example due to hydrophobic interactions, hydrogen bonds and ionic interactions.

Today various methods exist for identifying and verifying protein interactions in cells. The most common approach applied in the art is the two-hybrid system which may be conducted in yeast or E. coli (Escherichia coli). A drawback of said system is the detection of falls positive interaction due to wrong activation of reporter genes which may be due to the fact that human or other mammal proteins are analyzed in a yeast or E. coli system. In addition, the protein interaction may occur in an environment which does not equal the natural environment of the protein and protein interaction to be analyzed.

Another approach to identify protein interaction is co-precipitation of proteins out of cell extracts. However, said co-precipitation may give wrong results due to the fact that co-precipitation takes place in non-natural environmental conditions, like crude protein extract, different pH, different salt concentrations etc. Thus, artificial protein interaction may take place in the artificial cell extract which does not display the natural situation present in the cell. The same is true for another known approach, the so called pull-down assays. In a pull-down assay physical interactions between two molecules are used to separate the same from other components. In a pull-down assay a tag bait protein is captured on an immobilized affinity ligand specific for the tag, thereby generating a second affinity support for purifying other proteins that interact with the bait protein. Putative protein binding partners, the so called prey-proteins, may interact with the immobilized bait, thus, enabling verifying or identifying protein-protein interaction.

However, most of the above described systems are not useful for allowing in-vivo detection of protein interaction, due to the fact that they take place in artificial cell extracts.

Thus, there is still a demand for new methods and systems allowing the screening for and/or detection of molecule interaction and, in addition, there is an ongoing demand for methods allowing screening for and/or detection of SUMOylation of target molecules.

Hence, one object of the present invention is to provide a method for determining the ability of a molecule of interest to become SUMOylated. In addition, another object of the present invention is to provide a method for identifying specific interaction between a first predetermined binding molecule and a potential binding partner thereof or of binding multiprotein complexes.

These and other objects of the present invention can be derived from the description below.

BRIEF DESCRIPTION OF THE PRESENT INVENTION

In a first aspect, the present invention provides a method for determining SUMOylation of a molecule of interest comprising the steps of
  a. providing a first construct comprising Ubc9 or a homologue thereof having Ubc9 enzymatic activity and fused therewith a first moiety of a binding pair allowing for specific binding with the second moiety of said binding pair;
  b. providing the molecule of interest fused with said second moiety of the binding pair which specifically interacts with the first moiety of a binding pair fused with Ubc9 or a homologue thereof having Ubc9 enzymatic activity;
  c. optionally providing SUMO molecules being marked with a marker molecule;
  d. allowing binding of said first moiety of a binding pair with said second moiety of said binding pair;
  e. optionally, inducing binding between the two moieties of the binding pair in step d.) by providing a molecule inducing formation of a complex of the first moiety of said binding pair and the second moiety of said binding pair;
  f. determining conjugation of SUMO molecule(s) with the molecule of interest fused with the second moiety of said binding pair.

In a second aspect, the present invention relates to a method for screening and, optionally, identifying specific interaction between a first predetermined binding molecule and a binding partner thereof comprising the step of
  a) providing a first construct comprising Ubc9 or a homologue having Ubc9 enzymatic activity fused to the first predetermined binding molecule for which specific binding molecules should be detected;
  b) optionally providing SUMO molecules being marked with a marker molecule;
  c) allowing interaction between the binding molecule of the first construct with potential specific binding partners of said first binding molecule in an environment allowing binding of said binding partners and allowing SUMOylation of the binding partner after specific interaction between the first binding molecule and the binding partner; and
  d) detecting any SUMOylation of potential predetermined binding partners of the first binding molecule fused to Ubc9 or a homologue having Ubc9 enzymatic activity.

The environment allowing binding of the binding partners is in particular an environment resembling an in vivo environment, preferably, the environment is in vivo. The present invention allows determining trans-SUMOylation of a molecule of interest or a potential binding partner in particular under in vivo conditions.

Moreover, the present invention provides vectors comprising a nucleic acid molecule encoding a first peptide having an Ubc9 enzymatic activity and a nucleic acid molecule encoding a second peptide representing a first binding molecule which enables specific binding with a binding partner whereby the first peptide and the second peptide are fused to each other after translation in the polypeptide. Said binding partner is SUMOylated after specific interaction with the first binding molecule whereby binding is induced by providing a binding inducing molecule exogenously.

Further, the present invention discloses a system for determining SUMOylation of a molecule of interest as well as a system for detection of SUMOylation of a potential specific binding partner with the help of the SUMOylation pattern and, in addition, identifying a potential specific binding partner of a first predetermined binding molecule due to SUMOylation after specific interaction.

In addition, the present invention allow the determination of homologues of the Ubc9 enzyme having similar enzymatic activity, namely, mediating SUMOylation of molecules and the determination of homologues of the SUMO which can be conjugated by a Ubc9 homologue having Ubc9 enzymatic activity.

BRIEF DESCRIPTION OF THE DRAWINGS

FIG. 1 describes the SUMO pathway showing activation of the SUMO preform by the C-terminal hydrolase, E1-catalyzed SUMO activation and E2-catalyzed SUMO-conjugation to a substrate eventually mediated by E3 and, finally, deSUMOylation by deSUMOylases, thus, freeing the substrate from SUMO binding.

FIG. 2 shows a schematic representation of the Ubc9/substrate dimerisation-dependent SUMOylation system (USDDS). The USDDS system is representative of a system used in a method for determining SUMOylation of a molecule of interest described herein. That is, the SUMOylation substrate of interest is fused to one of the heterodimerisation domains, here FRB (FKBP12-rapamycin-associated protein), and the Ubc9 molecule is fused to the other domain, here FKBP (12 kDa-FK506-binding protein). When the fusion proteins are co-expressed in cells, incubation with the compound AP21967 (rapamycin derivative) induces heterodimerisation of the two fusion proteins. As a result, the SUMO loaded conjugating enzyme Ubc9 is brought in close proximity to the substrate molecule of interest and an effective SUMO conjugation of the substrate occurs.

STAT1-FRB=STAT1-FRB fusion protein conjugated with EGFP-SUMO1; E-S1-p53-FRB=p53-FRB conjugated with EGFP-SUMO1, E=EGFP-Tag; S-p53-FRB =p53-FRB conjugated with endogenous SUMO.

Figure 5:
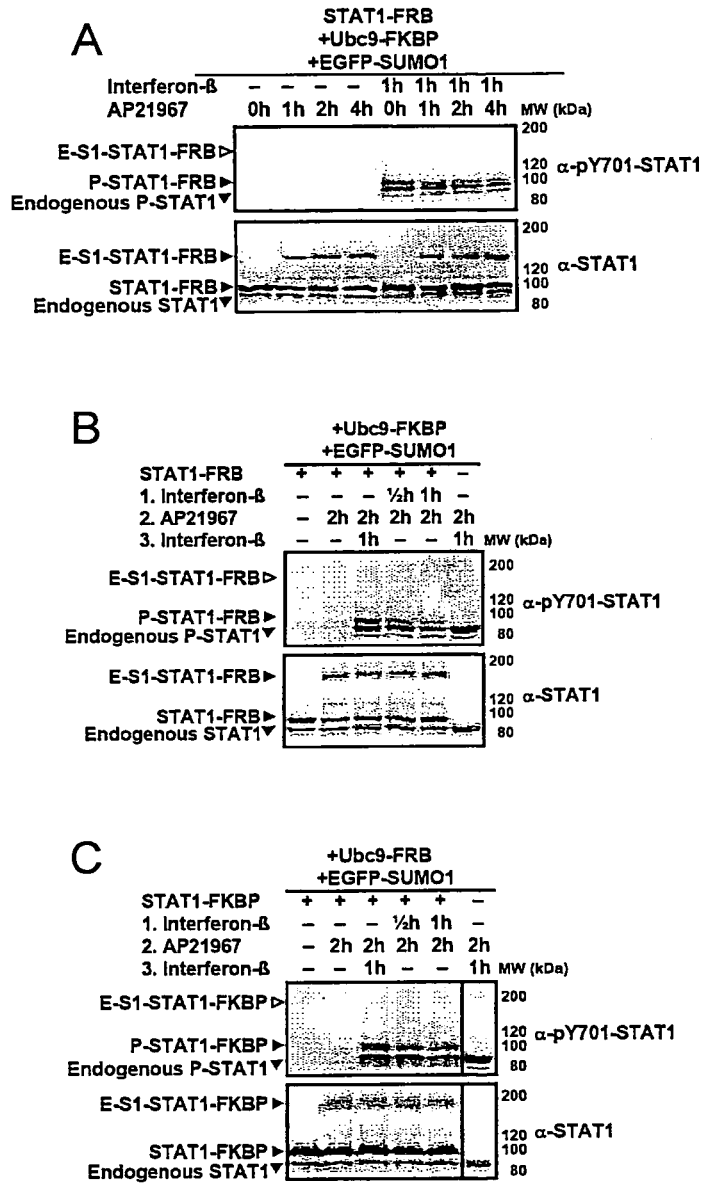

FIG. 5 Mutually exclusive in vivo phosphorylation of Y701 and SUMOylation of K703 in STAT1. (A, B, C) For USDDS, STAT1-FRB or STAT1-FKBP was coexpressed with Ubc9-FKBP or Ubc9-FRB and EGFP-SUMO1. (A) Transfectants were stimulated with interferon-β or left unstimulated (−) first and were subsequently treated with AP21967. (B,C) Transfectants were treated with AP21967 first and subsequently stimulated with interferon-β. The proteins of the transfectants were immunoblotted with a phospho (p)Y701 STAT1 antibody (α-pY701 STAT1), stripped and re-probed with a STAT1 antibody (α-STAT1). E-S1-STAT1-FRB or -FKBP=STAT1-FRB or -FKBP fusion protein conjugated with coexpressed EGFP-SUMO1, P-STAT1-FRB or -FKBP=STAT1-FRB or -FKBP phosphorylated at Y701, E=EGFP-Tag. E-S1-STAT1-FRB or -FKBP, P-STAT1-FRB or -FKBP, endogenous P-STAT1, STAT1-FRB or -FKBP and endogenous STAT1 are indicated by black arrow heads. In the upper blot the open arrow head indicates the positions of the E-S1-STAT1-FRB or -FKBP that are not decorated by the pY701-STAT1 antibody (α-pY701-STAT1).

Figure 6:
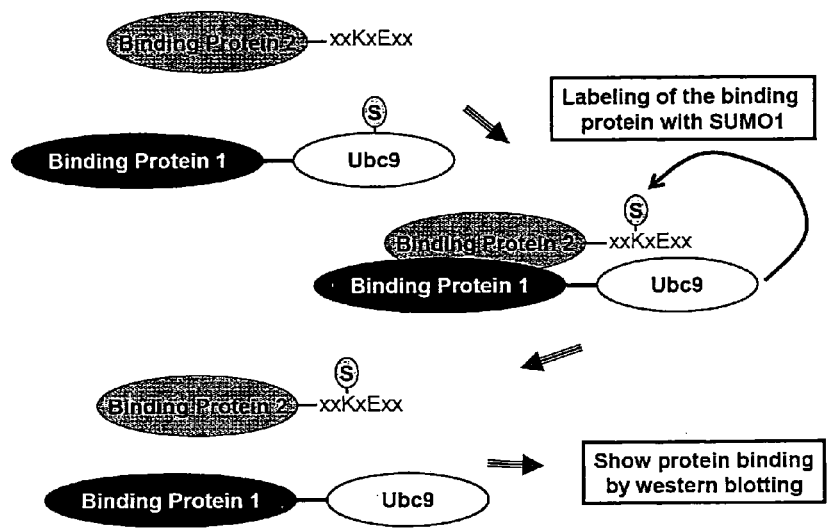
Figure 6:
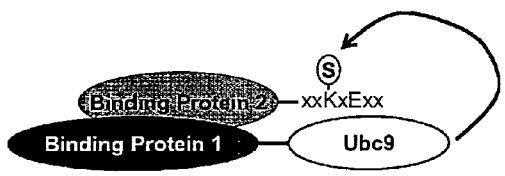
Figure 6:
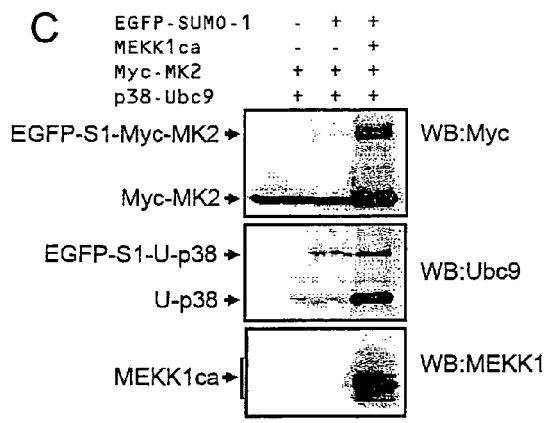
Figure 6:
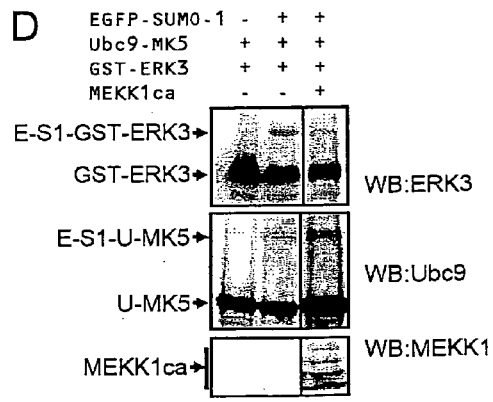
Figure 6:
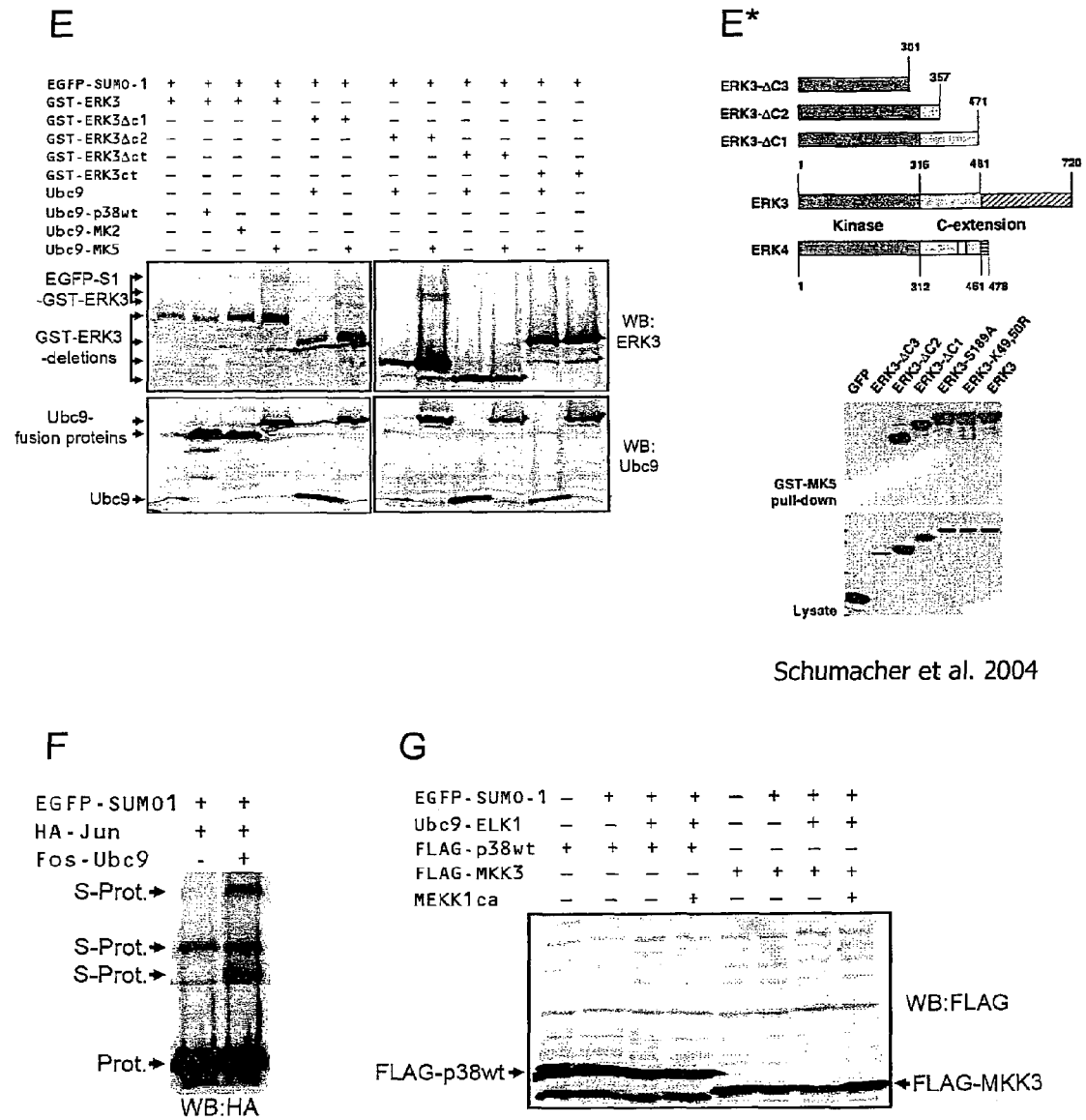

FIG. 6 The trans-SUMOylation system. A) A schematic representation of the trans-SUMOylation system. A binding protein 1 fused to Ubc9 binds specific with a coexpressed binding protein 2 that can be SUMOylated by the Ubc9 fused to the binding protein 1. This SUMOylation of binding protein 2 is dependent on an available SUMOylation site in binding protein 2 and on a direct interaction of binding protein 2 with binding protein 1. In vivo protein interaction can be monitored in a Western blot by a shifted band (SUMOylation) of binding protein 2. B) A schematic representation of the trans-SUMOylation of a binding protein 2 without natural SUMOylation site but fused to a SUMOylation consensus site. C-F) Examples for in vivo protein interaction shown by trans-SUMOylation. E*) Data about the binding of MK5 (MAP kinase-activated protein kinase 5) to ERK3 (Mitogen-activated protein kinase 6), which was shown in GST-pull down experiments (Schumacher et al., EMBO J., 2004,4770-4779). G) Examples for protein interactions, that have been described, that could not be shown with the trans-SUMOylation method. The indicated proteins were detected with specific antibodies for the fused FLAG (peptide sequence of the FLAG-tag is N-DYKDDDDK-C)-, HA (peptide tag of from the hemagglutinin protein)-, GST (Glutathione S-transferase tag has the size of 220 amino acids)- and Myc (peptide tag of from the cellular Myc protein)-tags. E-S1=EGFP-SUMO1, WB=Western Blot.

DETAILED DESCRIPTION OF THE PRESENT INVENTION

In the following, the term fused as used herein refers to a molecule or compound comprising two parts being fused with each other in a way that coexpression of the two parts occur. On the level of amino acids, a fused compound or fused molecule refers to a fusionpeptide, fusionpolypeptide or fusionprotein. That is, the peptide is expressed as a single polypeptide comprising the at least two parts. On the level of nucleic acids, the term "fused" or "fusion" refers to nucleic acids molecules which are operably linked with each other, thus, resulting in a transcript comprising the two parts of the fusionpeptide, fusionpolypeptide or fusionprotein, respectively.

The term "binding pair" as used herein refers to a complex of at least two binding molecules also referred to as binding moieties, namely a first moiety of the binding pair and a second moiety of the binding pair. Binding molecule and binding moiety are used herein interchangeably.

The term SUMOylation as used herein refers to a process in which a SUMO molecule is conjugated to a target protein. On the level of amino acids, the carboxy group of the C-terminal glycine of the mature SUMO protein builds an isopeptide bond with the ε-amino group of the lysine in the SUMOylation site of the target protein.

The term "Ubc9" as used herein, refers to the Ubc9 protein or a peptide or a nucleic acid encoding the same, in particular, a polypeptide displaying Ubc9 enzymatic activity of conjugating SUMO at an appropriate site of a target molecule, for example the DNA and polypeptide of Seq. ID Nos. 5 and 6, respectively, corresponding to the human Ubc9 protein. A homologue thereof having Ubc9 enzymatic activity refers to molecules enabling conjugation of SUMO at an appropriate site of a substrate.

In a first aspect, the present invention provides a method for determining SUMOylation of a molecule of interest. Said method comprises the steps of
a) providing a first construct comprising Ubc9 or a homologue thereof having Ubc9 enzymatic activity and fused therewith a first moiety of a binding pair allowing for specific binding with the second moiety of said binding pair;
b) providing the molecule of interest fused with said second moiety of the binding pair which specifically interacts with the first moiety of a binding pair fused with Ubc9 or a homologue thereof having Ubc9 enzymatic activity;
c) optionally providing SUMO molecules being marked with a marker molecule;
d) allowing binding of said first moiety of a binding pair with said second moiety of said binding pair;
e) optionally, inducing binding between the two moieties of the binding pair of step d.) by providing a molecule inducing formation of a complex of the first moiety of said binding pair and the second moiety of said binding pair;
f) determining conjugation of SUMO molecule(s) with the molecule of interest fused with the second moiety of said binding pair.

That is, binding of said first moiety with said second moiety to form a binding pair may occur without being mediated by a third compound, like a molecule inducing formation of a complex, e.g. a receptor and ligand, or by adding a molecule inducing formation of a binding complex, e.g. the FRB/FFKBP/rapamycin-System as described herein.

In another aspect, the present invention relates to a method allowing screening and, optionally, identifying specific interaction between a first predetermined binding molecule and a potential binding partner thereof. Said method comprises the step of
a) providing a first construct comprising Ubc9 or a homologue having Ubc9 enzymatic activity fused to the first predetermined binding molecule for which specific binding molecules should be detected;
b) optionally providing SUMO molecules being marked with a marker molecule;
c) allowing interaction between the binding molecule of the first construct with potential specific binding partners of said first binding molecule in an environment allowing SUMOylation of the binding partner after specific interaction between the first binding molecule and the binding partner; and d) detecting SUMOylation of potential predetermined binding partners of the first binding molecule fused with Ubc9 or a homologue having Ubc9 enzymatic activity.

Advantages of the present methods allowing determination of protein interaction using the trans-SUMOylation system according to the present invention include the determination of in vivo interaction between two or more molecules, in particular, between two or more proteins to be analyzed.

Moreover, since SUMOylation of the interacting binding partners may take place only after interaction in vivo or under predetermined conditions in a cell-free in-vitro system, later SUMOylation of molecules during the subsequent cell lysis can be excluded, thus, excluding artificial SUMOylation and false results. This unwanted artificial SUMOylation may be excluded further by using modified SUMO or enzyme having Ubc9 activity or applying conditions inhibiting the desymoylase.

Thus, unwanted interaction between molecules, like protein interaction which occur during protein extract preparation during detection of SUMOylation, can be excluded. In addition, well established and simple methods may be applied when detecting SUMOylation of potential binding partners or of the molecule of interest. For example, determination or detection of the molecule of interest and the binding partner, respectively, may be achieved by Western Blot Analysis or by detecting a mobility shift in a gel due to SUMOylation of the molecule. In a preferred embodiment, detection of SUMOylated molecules of interests or binding partners may be effected using binding partner specific antibodies and/or SUMO specific antibodies.

In addition, in a preferred embodiment the method further comprises the step of providing SUMO molecules to the system. Said SUMO molecules are modified by containing a marker component. Said marker component may any one of marker components known in the art and including the use of radioactive isotopes, fluorescent molecules, enzymatic activity, peptide tags etc. Said SUMO molecules are possibly also modified to inhibit deSUMOylation. That is, the SUMO molecules may be modified to decrease a deSUMOylation in vivo. For example the molecules may be modified by adding a prolin residue at the 4-C-terminal position. Thus, the SUMO-protease activity is inhibited. Preferably, the SUMO molecules which may be provided exogenously is a Luciferase-SUMO construct. Further, the SUMO-molecules which may be provided exogenously into the test system is modified by containing a tag allowing purification of the SUMO molecules, in particular, of molecules to which said modified have been attached to by Ubc9 activity. This tag is preferably selected from the group of a STREP-group, a GST-group, a bioease-group or protein-A-tag.

That is, in a preferred embodiment, the SUMO molecules and/or the Ubc9 molecules are provided from a heterologous source for the test system. For example, the SUMO molecules and/or the Ubc9 molecules are xenogenic molecules, like molecules derived from the yeast system and applied in a mouse or human system or vice versa. This may be in particular useful when excluding endogenous SUMO molecules and/or endogenous Ubc9 activity. Alternatively or in combination with the above heterolog molecules, mutants, i.e. modified SUMO or Ubc9 may be used. For example SUMO may be modified as outlined above and/or the enzymatic activity may be modified insofar that only SUMO molecules are conjugated with the molecule of interest or the potential binding partners which is supplied from exogenous sources.

Thus, it is preferred that the exogenously added SUMO is not processed by endogenous Ubc9 enzyme and/or that the Ubc9 enzyme introduced into the system does not use endogenous SUMO as a substrate.

In case the binding partner itself does not contain a suitable SUMOylation site, said binding partners may be modified by fusion of a domain comprising a SUMOylation site, e.g. a SUMOylation site as described in the art. In an embodiment of the inventions, at least two, e.g. two, three, four or more domains comprising a SUMOylation site may be added to the binding partner, e.g. the molecule of interest or the potential binding partners.

The methods according to the present invention may be conducted in vivo with mammalian cells transfected with the construct containing the Ubc9 or a homologue having Ubc9 enzymatic activity fusion molecule as described herein. Alternatively, the method may be used in cell free system, however, preferably, the method according to the present invention are performed in vivo. Thus, the molecules of interest or the potential binding partners are modified with a domain comprising a known SUMOylation site. For example, said SUMOylation site is the SUMOylation site as described below.

Further, in one embodiment, the SUMO molecule itself which may be supplied from exogenous sources may contain additional SUMOylation sites, thus, amplification of the signal due to the formation of di-, tri-, or higher multimers is possible.

That is, a cell line may be transfected with a first construct comprising a nucleic acid molecule encoding a peptide having Ubc9 enzymatic activity and a second nucleic acid molecule encoding a second peptide, representing the first binding molecule which enables specific binding with the binding partner which may be SUMOylated due to the interaction with the first binding molecule. The two peptides are fused with each other, thus, providing a polypeptide or fusionprotein containing a first peptide moiety having Ubc9 enzymatic activity and a second peptide moiety representing a binding moiety whereby binding is induced by providing a binding inducing molecule exogenously.

In one embodiment of the present invention, the transfected cell line transfected with the first construct may be transfected with a second construct. Said second construct contains the molecule of interest, and encodes a fusion construct comprising the molecule of interest with the second moiety of said binding pair. In a preferred embodiment, the first moiety of the binding pair enabling an induced heterodimisation of both moieties of binding pairs is the FKBP-encoding peptide and the second moiety of the binding pair enabling an induced heterodimerisation of both moieties of binding pairs is the FRB-encoding peptide. By an addition of e.g. rapamycin or derivatives thereof, a heterodimer-formation is induced between the 12 kDa-FK506-binding protein (FKBP12) or derivatives thereof and the FKBP12-rapamycin-associated protein (FRB) or derivatives thereof which together form a relatively stable ternary complex (Choi et al., Science, 1996, 239-242).

Derivatives of rapamycin, FKBP or FRB mean compounds or polypeptides having the same functionality as the respective compounds.

Thus, a particular preferred embodiment relates to a method, comprising the step of a.) providing a first construct comprising Ubc9 or a homologue having Ubc9 enzymatic activity and fused to FKBP which represents a first moiety of a binding pair allowing for a specific binding with the second moiety with the binding pair;

b.) providing the molecule of interest fused with FRB representing the second moiety of the binding pair, which specifically interacts with the first binding molecule fused with Ubc9 representing the first moiety of a binding pair;

c.) inducing heterodimer-formation of FKBP and FRB by providing rapamycin or a derivative thereof;

d.) determining any SUMO molecules present on the molecule of interest.

In a further aspect the present invention dislcoses a recombinant protein comprising a first peptide having Ubc9 enzymatic activity and a second peptide allowing specific interaction with the binding part of interest is provided.

Preferably, said recombinant protein allows specific interaction of the binding partner comprising a peptide moiety allowing specific interaction with the binding peptide present in the recombinant protein according to the present invention after providing a heterodimer forming inducible molecule.

Particular preferred, the second peptide of the recombinant protein allowing specific interaction with a binding partner of interest is the FRB domain or derivative thereof and the binding partner comprises the FKBP domain or derivative thereof while the molecule inducing heterodimer formation is rapamycin or derivative thereof.

In a further aspect, the present invention relates to a system allowing screening and/or determining SUMOylation of a molecule of interest. Said system comprises at least the following components: i) a first construct comprising Ubc9 or a homologue having Ubc9 enzymatic activity in form of a nucleic acid encoding the Ubc9 protein or in form of a peptide wherein said peptide display an Ubc9 enzymatic activity. Said Ubc9 or a homologue having Ubc9 enzymatic activity is fused with a first moiety of a binding pair allowing for specific binding with the second of said binding pair or the nucleic acid encoding the same. Further, the system contains ii) a second construct allowing fusion of a molecule of interest with said second moiety of said binding pair. Optionally, a means for determination of SUMOylation is present in the system. The system may be in form of a kit. Said system may additionally contain instructions for use of said system allowing determination of SUMOylation of a molecule of interest.

This system may also allow the screening and/or detection of potential molecules, like peptides, having Ubc9 enzymatic activity, namely, mediating the conjugation of SUMO with substrates. Thus, homologues of the Ubc9 molecules from other species may be identified. In addition, the use of homologues of the Ubc9 enzyme having a different enzymatic specificity in a system or method according to the present invention using SUMO molecules other than the SUMO molecules naturally present in the system allows determining specific binding partners in the natural environment.

In still another aspect, the present invention relates to a system for detection of SUMOylation of a potential specific binding partner of a first predetermined binding molecule. Said system comprises i) a first construct comprising Ubc9 in form of a nucleic acid molecule encoding Ubc9 enzymatic activity and ii) a means for introducing the first predetermined binding molecule into said first construct, thus, resulting in a construct containing Ubc9 fused with said predetermined binding molecule. The system additionally contains SUMO molecules containing a marker moiety and optionally, means for detection of SUMOylation of potential binding partners of the first predetermining binding molecule.

In preferred embodiments of said system, the system additionally contains means for fusion the potential binding partners with a domain containing a SUMOylation site.

Another preferred embodiment relates to a system further comprising a heterodimer formation inducing molecule interacting specifically with the first binding moiety and the second binding moiety of said binding pair, thus, allowing formation of said binding pair.

Particularly preferred, said heterodimer formation inducing molecule is the rapamycin-derivative, AP2196.

In a preferred embodiment, the first construct containing Ubc9 or a homologue having Ubc9 enzymatic activity and fused to the first binding molecule is provided in form of a vector construct or as a cell line containing said construct.

Finally, the present invention concerns the use of the construct according to the present invention comprising Ubc9 or a homologue having Ubc9 enzymatic activity and fused therewith a first moiety of a binding pair allowing for specific binding for a second moiety of said binding pair as a screen tool for an agent for preventing or treating specific diseases. Said diseases disorders or pathogenic conditions compromise diseases and disorders like cancer and inflammation.

The use of said compounds as a screen tool allows detection of agents altering the SUMOylation of specific binding partners, thus, showing a changed protein interaction, e.g. due to the action of the agent etc. Further, the system and method as described herein allows the screening of molecules, in particular of peptides, having enzymatic activity of conjugating SUMO at a substrate.

In one embodiment, said agent may inhibit SUMOylation of said binding partner, in another embodiment, SUMOylation of said binding partner is increased while other post-translational modifications may be altered as well.

The method according to the present invention allows determining trans-SUMOylation in vivo or an environment resembling the in vivo situation due to molecule interaction and particular protein interaction. Thus, in vivo binding between proteins can be demonstrated in e.g. mammal cells.

In another embodiment of the present invention, the binding partner of a first predetermined binding molecule may further be purified by known techniques based on the SUMOylation after interaction with the binding molecule. For example, the potential binding partners or the molecule of interest has a tag, in particular a tag selected from the group of a STREP-group, a GST-group, a bioease-group or protein-A-tag. These tags allow identification and/or purification of the molecules. Since the methods according to the present invention can be conducted in vivo in the natural environment of mammal cells, specific SUMOylation can be obtained.

Thus, the advantages of the present invention are:

a) identification of protein interaction in e.g. mammal cells in vivo.

b) exclusion of artificial interaction due to non-natural binding conditions present e.g. in hosts other then the natural host e.g. yeast or *E. coli* or due to artificial conditions present at protein interaction.

c) in contrast to co-immunoprecipitation techniques that show protein association, the SUMO protein is covalently linked with the binding partner. In addition, during further analysis or purification, SUMO proteases should be inhibited and, in addition, any SUMOylation activity, thus, SUMOylation allows identifying binding partners where protein interaction occurs in natural environment.

Further, the methods according to the present invention allow specific manipulation of protein complexes in a cell regulated by SUMOylation. For example, inhibitors may be identified inhibiting or promoting trans-SUMOylation of a binding partner. Thus, the vector and recombinant proteins described herein are useful as research tools for identifying valuable agent allowing to prevent or to treat pathogenic diseases.

The use of a construct comprising Ubc9 or a homologue having Ubc9 enzymatic activity and fused therewith a first a moiety of a binding pair allowing for specific binding with the second moiety of said binding pair wherein the construct is either a nucleic acid molecule, a vector containing said nucleic acid molecule or a recombinant protein, as a screening tool enables screening of pharmaceutically valuable agents allowing for treating or preventing pathogenic diseases. Said diseases and or disorders or conditions comprise cancer and inflammation. When the construct according to the present invention is a peptide molecule, said peptide molecule may further contain commonly known peptide sequences allowing the transport said recombinant peptides into the cells and, in particular into specific cell components, like the nucleus. Typical examples of said peptide moiety include the TAT (protein von HIV-1) sequences or VP22 (protein of the herpes simplex virus) etc.

The present invention may also allow determining ubiquitination of molecules of interest and of specific binding partners of predetermined binding molecule.

Thus the present invention relates further to methods allowing screening and/or determination of ubiquitination of a molecule of interest comprising step of
a) providing a first construct comprising an enzyme having an ubiquitination activity and fused therewith a first binding molecule which represents a first moiety of a binding pair allowing for specific binding with the second moiety of said binding pair;
b) providing the molecule of interest fused with said second moiety of the binding pair which specifically interacts with the first binding molecule fused with the enzyme having ubiquitination activity representing the first moiety of a binding pair;
c) optionally providing ubiquitin molecules being marked with a marker molecule;
d) allowing binding of said first moiety of a binding pair with said second moiety of said binding pair;
e) optionally inducing binding between the two moieties of the binding pair according to step d) by providing a molecule inducing formation of a binding pair of the first moiety of said binding pair and the second part of said binding pair;
f) determining conjugation of ubiquitination molecule(s) with the molecule of interest.

In a further aspect, the present invention relates to a method for screening and, optionally, identifying with specific interaction between a first predetermined binding molecule and binding partner thereof comprising
a) providing a first construct comprising an enzyme having a ubiquitination activity and fused therewith a first binding molecule which represents a first moiety of a binding pair allowing for specific binding with the second moiety of said binding pair;
b) providing the molecule of interest fused with said second moiety of the binding pair which specifically interacts with the first binding molecule fused with an enzyme having ubiquitination activity representing the first moiety of a binding pair;
c) optionally providing ubiquitin molecules being marked with a marker molecule;
d) allowing binding of said first moiety of a binding pair with said second moiety of said binding pair;
e) optionally inducing binding between the two moieties of the binding pair according to step d) by providing a molecule inducing formation of a binding pair of the first moiety of said binding pair and the second part of said binding pair;
f) determining conjugation of ubiquitination molecule(s) with the molecule of interest.

Using the present method and system allow to determine specific SUMOylation or ubiquitination after interaction of the binding partners. Using the disclosed methods, analysis of post-translational modification patterns is possible. In particular, it is possible to determine the influence of e.g. phosphorylation on later SUMOylation and vice versa. The same is true for the interaction of other posttranslational modifications mentioned above. As shown in the examples below, for the STAT1 molecule Y701 phosphorylation and K703 SUMOylation are mutually exclusive.

The analysis of the different modification of one protein will be facilitated with the methods and systems according to the present invention. The USDDS system described herein combines the effective and specific SUMOylation system described in the art with an inducible heterodimerisation that make it possible to reach control to the SUMOylation of a subject protein at any time point within a sequential scenario of modification events.

Thus, the method according to the present invention will be essential for studying the kinetics and the dynamic interplay of protein SUMOylation with other posttranslational modifications.

In addition the second embodiment of the present invention, namely the method for identifying a specific interaction between a first predetermined binding molecule and a binding partner thereof allows identifying new binding molecules of the first predetermined binding molecule and provides further insights in the protein interaction in mammalian cells in vivo.

Furthermore, the trans-SUMOylation system (TRS) according to the present invention allows to identify and define binding and dimerisation or multimerisation in vivo.

In the following, the present invention will be further illustrated by the examples below. It is clear that the present invention can not be construed to be restricted thereon.

EXAMPLES

Example 1

Ubc9/Substrate Dimerisation Dependent SUMOylation (USDDS)

Figure 1:
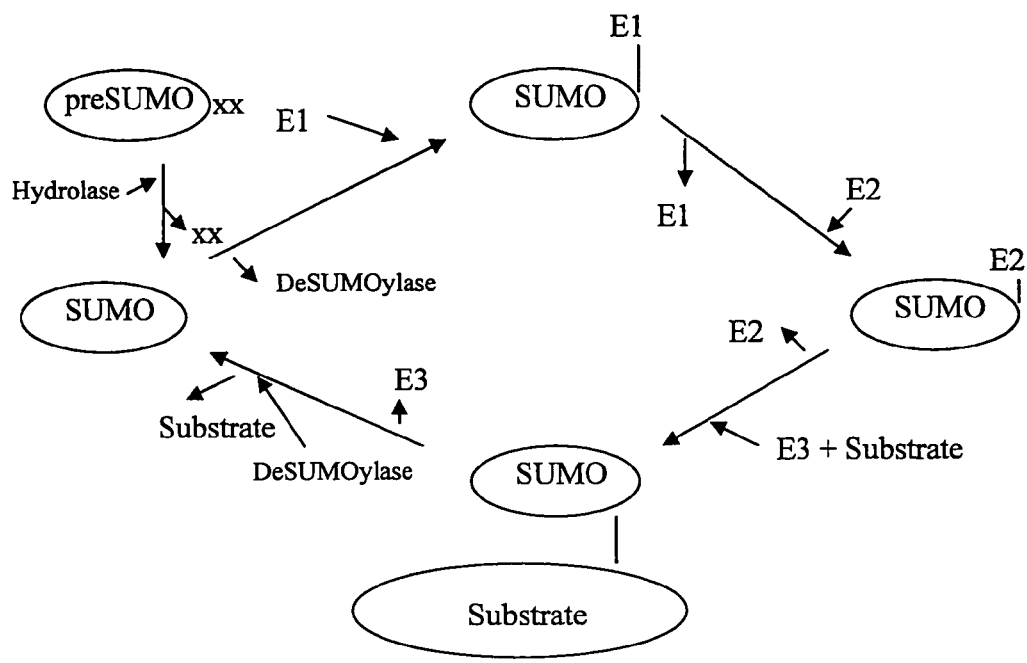
FIG. 1.
Figure 2:
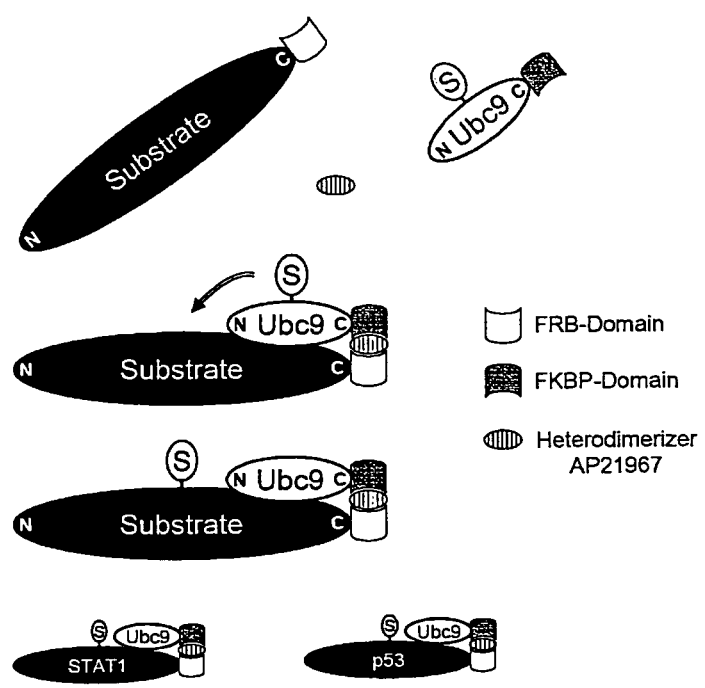
FIG. 2.

To identify new SUMOylation substrates and to study the function of SUMOylation the Ubc9/substrate dimerisation-dependent SUMOylation system (USDDS) was developed which consists of fusions of the SUMOylation substrate and of the SUMO-conjugating enzyme Ubc9 to the chemically activatable heterodimerisation domains FKBP and FRB, respectively, as shown in FIG. 2. When the substrate protein fused to FKBP is coexpressed with Ubc9-FRB, treatment of HEK293 cells with the rapamycin-related dimerizer AP21967 induces SUMOylation of the substrate protein fused to FKBP at its specific SUMOylation site. To establish this system the cDNA encoding for the FKBP-domain from pC4EN-F1E and the FRB (T2098L)-domain from pC4-RHE (ARGENT Regulated Heterodimerization Kit) were amplified by PCR using the primers FKBP-EcoR1 (5'-GCGC-GAATTCTCCAGAGGAGTGCAGGTGGAAACCATC-3') (Seq. ID No. 1) and FKBP-Xbal (5'-GCGCTCTAGAT-TAACTAGTTTCCAGTTTTAGAAGCTC-3') (Seq. id: No: 2) or the primers FRB-EcoR1 (5'-GCGCGAATTCTCCA-GAATCCTCTGGCATGAGATGTGG-3') (Seq. ID No. 3) and FRB-Xbal (5'-GCGCTCTAGATTAAC-TAGTCTTTGAGATTCGTCGGAACACAT-GATA-3') (Seq. ID No. 4) and cloned it together with the BamHl/EcoR1 cDNA fragment encoding human STAT1a or the BamHI/EcoRl cDNA fragment coding for human p53 into the BamHl and Xbal sites of pcDNA3 (Invitrogen) to generate the mammalian STAT1-FKBP/FRB and the p53-FKBP/FRB expression vectors. Dependent on an EcoRI site in the coding sequence, seven C-terminal amino acids of the human STAT1a in the STAT1-FKBP/FRB fusion proteins are missing. For the SUMOylation analysis HEK293 (human embryonic kidney cells) cells have been used. HEK293 cells were cultured in Dulbecco's modified Eagle's medium with high glucose, complemented with 10% fetal calf serum, 2 mM L-glutamine, 100 U/ml penicillin and 100 mg/ml streptomycin. We performed transfection of HEK293 cells using the polyethylenimine transfection reagent. HEK293 cells of a fresh confluent 10 cm plate were transferred on a 12-well plate. After 12-24 h incubation about 70% cell confluence is reached. For each well 45 µl of serum/antibiotic free DMEM medium is mixed with 750 ng of the transfection-purity expression vector DNA (all together 47 µl) and vortexed. Then, 3 µl of vortexed polyethylenimin stock solution (1 mg/ml) is added and the mixture is vortexed. After incubation at room temperature for 10 min 450 µl fresh DMEM with antibiotics is added to the mixture and vortexed. The medium on the cells was then completely removed and immediately, the 500 µl transfection mix was added carefully to each well. The 12 well plate was rocked to ensure a proper distribution of the DNA/transfection reagent complex. After an incubation of the cells for 24 h at a 37° C. in a humidified CO2-incubator (5%) the cells were lysed in 150 µl Laemmli (2×) gel loading buffer (160 mM Tris-HCL, pH 6.8, 4% (w/v) sodium dodecyl sulphate (SDS), 20% (v/v) glycerol, 0.5% β-mercaptoethanol (v/v), 0.008% (w/v) bromophenol blue) and incubated for 10 min at 95° C. For western blot analysis the proteins were separated by SDS-PAGE, blotted on a PVDF membrane and developed with specific primary antibodies (α-Ubc9 (H81, Santa Cruz), α-pY701-STAT1 (Tyr701, Cell Signaling), α-STAT1 (Cell Signaling), α-p53 (1C12, Cell Signaling), α-SUMO1 (Cell Signaling), a horseradish peroxidase (HRP)-conjugated secondary antibody (different companies), the ECL+ (Amersham) or Immobilon™ Western (Millipore) and the LAS-3000 imaging system (Fuji).

SUMOylation by Induced Heterodimerisation.

Figure 3:
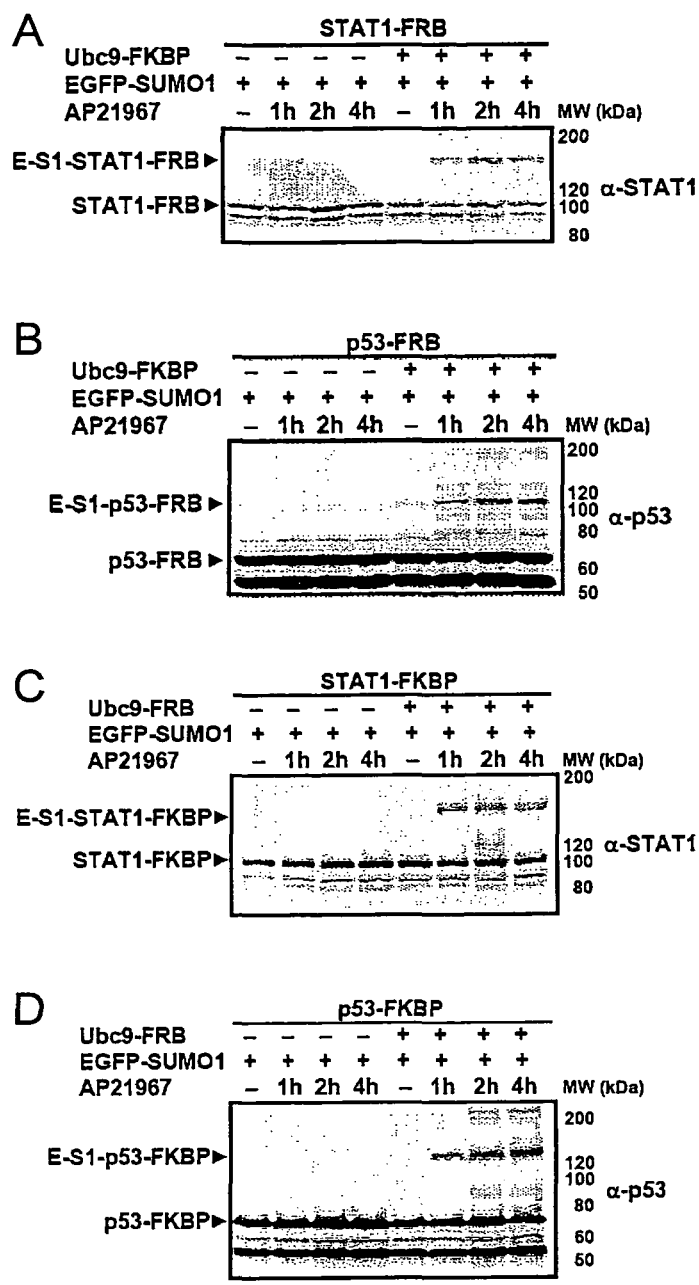
FIG. 3 AP21967-induced in vivo SUMOylation of STAT1 and p53. (A) STAT1-FRB and EGFP (enhanced green fluorescent protein)-SUMO1 or (B) p53-FRB and EGFP-SUMO1 were coexpressed either alone (−) or together with Ubc9-FKBP (+) and (C) STAT1-FKBP and EGFP-SUMO1 or (D) p53-FKBP and EGFP-SUMO1 were coexpressed either alone (−) or together with Ubc9-FRB (+). After stimulation with the AP21967 the fusion proteins were detected by western blot using (A and C) a STAT1 antibody (α-STAT1) or (B and D) a p53 antibody (α-p53). E-S1-STAT1-FRB(FKBP) =STAT1-FRB(FKBP) fusion protein conjugated with EGFP-SUMO1; E-S1-p53-FRB(FKBP)=p53-FRB(FKBP) conjugated with EGFP-SUMO1, E=EGFP-Tag.

When p53-FRB or STAT1-FRB were coexpressed with Ubc9-FKBP together with EGFP-SUMO1, no significant EGFP-SUMO1 conjugation of STAT1-FRB and of p53-FRB could be detected (FIG. 3A,B). In contrast, incubation of the transfectants with the dimerizer AP21967 (1 µM) for the indicated times leads to a strongly enhanced SUMOylation of STAT1-FRB and p53-FRB (FIG. 3A,B). Further, STAT1-FKBP and p53-FKBP in combination with Ubc9-FRB was tested. Again, AP21967-induced SUMOylation of the FKBP-fusion proteins has been found (FIG. 3C,D). Fusion proteins in the extracts of the transfectants were detected by western blots using a STAT1 antibody (α-STAT1) or a p53 antibody (α-p53).

Example 2

Figure 4:
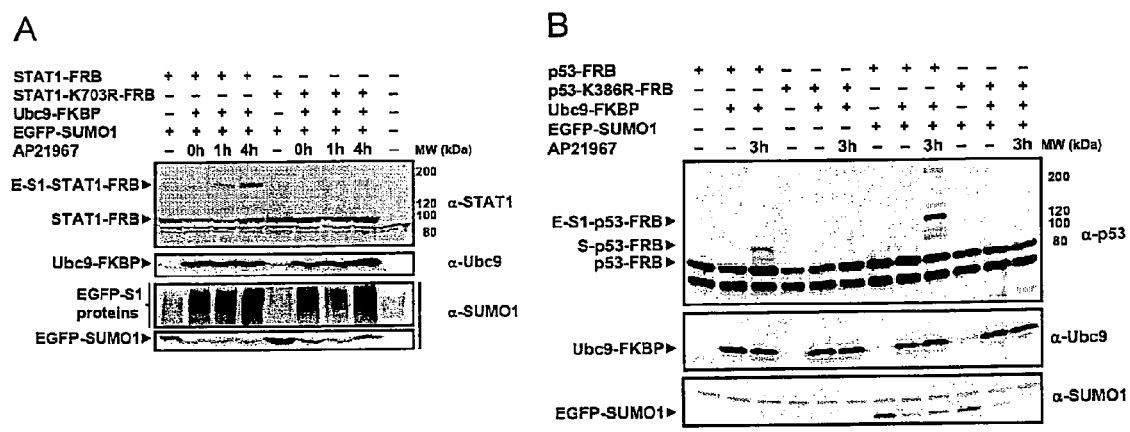
FIG. 4 USDDS results in SUMOylation of STAT1 and p53 at their specific SUMOylation sites. EGFP-SUMO1 and (A) STAT1-FRB or STAT1-K703R-FRB, (B) p53-FRB or p53-K386R-FRB were coexpressed either alone (−) or together with Ubc9-FKBP (+). After stimulation with AP21967 the fusion proteins were detected by western blot using (A) a STAT1 antibody (α-STAT1) or (B) a p53 antibody (α-p53). After stripping the Ubc9-FKBP was detected with the Ubc9 antibody (α-Ubc9) and after a second stripping EGFP-SUMO1 and SUMOylated proteins (EGFP-S1 proteins) were detected with the SUMO1 antibody (α-SUMO1). E-S1-

USDDS Results in SUMOylation of STAT1 and p53 at their Specific SUMOylation Sites To prove that USDDS displays specificity for the in vivo SUMOylation sites of p53 and STAT1, we coexpressed the mutant proteins p53K386R-FRB and STAT1K703R-FRB with Ubc9-FKBP and EGFP-SUMO1. After 24 h the cells were stimulated with AP21967 (1 µM) for the indicated times. Fusion proteins in the extracts of the transfectants were detected by western blot using a STAT1 antibody (α-STAT1) or a p53 antibody (α-p53). After stripping the Ubc9-FKBP was detected with the Ubc9 antibody (α-Ubc9) and after a second stripping EGFP-SUMO1 and SUMOylated proteins (EGFP-S1 proteins) were detected with the SUMO1 antibody (α-SUMO1). In HEK293 cells nearly no SUMOylation of STAT1K703R-FRB (FIG. 4F) and of p53K386R-FRB (FIG. 4G) was identified. Obviously, the induced heterodimerisation of the Ubc9 fusion protein with the substrate fusion proteins leads preferentially to a modification at their specific SUMOylation sites.

Example 3

Mutually Exclusive in vivo Phosphorylation of Y701 and SUMOylation of K703 in STAT1

The USDDS was used to study the interplay of Y701 phosphorylation and the K703 SUMOylation in vivo (FIG. 5). Therefore, STAT1-FRB and Ubc9-FKBP were coexpressed in HEK293 cells. After 24 h the transfectants were stimulated with interferon-(½ h or 1 h) to induce STAT1 phosphorylation or left unstimulated (−) and subsequently treated with AP21967 (1 µM) to induce STAT1 SUMOylation. In further experiments the transfectants were treated (2h) with AP21967 (1 µM) first and subsequently stimulated with interferon-β (1 h). The proteins of the transfectants were immunoblotted with a phospho (p)Y701 STAT1 antibody (α-pY701 STAT1), stripped and re-probed with a STAT1 antibody (α-STAT1) to detect also non-phosphorylated and SUMOylated STAT1. The proteins of the transfectants then were analyzed by a pY701-STAT1 specific antibody, that recognizes the tyrosine 701 phosphorylation also in SUMOylated STAT1 (FIG. 5). The interferon-β stimulation induced Y701 phosphorylation of endogenous STAT1 and of the STAT1-FRB fusion protein. However, pY701 could never be detected in the gel region where SUMOylated STAT1-FRB migrates. In contrast a subsequent western blot using a STAT1 specific antibody clearly detects SUMOylated STAT1-FRB (FIG. 5). Hence, STAT1 phosphorylation at Y701 excludes K703 SUMOylation. Then USDDS was applied to analyze the influence of K703 SUMOylation on Y701 phosphorylation of both STAT1-FRB and STAT1-FKBP (FIG. 5B,C) Western blot analysis of the transfectants for the STAT1-FRB (FIG. 5B) or STAT1-FKBP (FIG. 5C) revealed that no double modification of STAT1 by SUMOylation and Y701 phosphorylation is detectable under any of the stimulation scenarios although single Y701 phosphorylation or SUMOylation are clearly detectable. Hence, USDDS clearly reveals that STAT1 SUMOylation and STAT1 phosphorylation at Y701 are mutually exclusive (FIG. 5) supporting a model of preventing signal integration at STAT1 and probably ensuring the existence of differentially modified subpopulations of STAT1 necessary for its regulated nuclear cytoplasmic activation/inactivation cycle.

Example 4

Trans-SUMOylation Monitors Protein-Protein Interaction

As shown above, the SUMOylation of a protein of interest can be induced by the heterodimerisation with a binding protein fused to Ubc9. To find out if Trans-SUMOylation is useful for the characterisation of common protein interactions, protein binding pairs well known from the literature or found in two hybrid screens. MK2/p38, MK5/ERK3, Jun/Fos, ELK1/p38 and ELK1/MKK3 were analyzed for trans-SUMOylation (FIG. 6). Therefore the protein pairs were coexpressed with EGFP-SUMO1 in HEK293 cells and after 24h the transfectants were lysed and the protein extracts were analyzed in western blots. It was found out that trans-SUMOylation confirms the binding pairs MK2/p38, MK5/ERK3 and Jun/Fos (FIG. 6C,D,E,F). Trans-SUMOylation could not be shown for ELK1/p38 and ELK1/MKK3 (FIG. 6G).

Trans-SUMOylation Identifies Interaction Domains

To verify the usability of the trans-SUMOylation system, it was tested if the system also can be used to characterize protein interacting domains. Therefore the binding of MK5 to ERK3 was studied more detailed with the trans-SUMOylation system. Therefore MK5-Ubc9 was coexpressed with ERK3 deletion mutants fused to GST (FIG. 6E). As found out the data clearly resembled the MK5/ERK3 interaction as it was described by Schumacher et al., EMBO J., 2004, 4770-4779.

Trans-SUMOylation of a SUMOylation Site Tag.

The data of the interaction between MK5 and ERK3 obtained with the trans-SUMOylation system, also can be interpreted in a way, that the deletion of ERK3 has removed the SUMOylation site necessary in ERK3 for trans-SUMOylation. Furthermore the trans-SUMOylation only should work if a SUMOylatable site is available in the protein. To make the trans-SUMOylation system usable also for proteins without a SUMOylation site, the use of a fused SUMOylation site tag to monitor a protein/protein interaction was tested. Therefore the p53 for which a trans-SUMOylation by the CSNK2B-Ubc9 fusion protein has been shown, was used. To test the functionality of a SUMOylation site Tag the p53K386R, which could not be SUMOylated by CSNK2B-Ubc9 was used and the SUMOylation site tag n-TSRH-KKLMFKTEGPDSD-c (Seq. ID. No. 7) known from p53 to be SUMOylated was fused to it. While the coexpression of the p53K396R with the CSNK2B-Ubc9 shows no p53 SUMOylation, the addition of the SUMOylation site tag, fused with no, 3xglycin or a 6x glycin linker showed significant SUMOylation, and in this way demonstrate the interaction of p53 with CSNK2B. Moreover, even a tag of 8 amino acids of Seq. ID. No. 8 (MFKTEGEG) represents a functional SUMOylation-tag.

In tables 1 and 2, the results for various protein-protein interactions determined with the method of trans-SUMOylation according to the present invention are described.

TABLE 1A

Protein-protein interactions verified by Trans-SUMOylation

| Protein 1 | Protein 2 | Reference | Protein1 fusions to Ubc9 | Protein2 constructs and mutants thereof | Trans-SUMOylation |
|---|---|---|---|---|---|
| CDC37 | CDK4 | Stepanova L (1996), Ewing R M (2007), Dai K (1996), Lamphere L (1997) | U-CDC37<br>CDK4-U | GST-CDK4<br>GST-CDC37 | +<br>+ |
| CSNK2B | CSNK2B | Lehner B (2004), Kim M S (1998), Marin O (1997), Niefind K (2000), Niefind K (2001), Gietz R D (1995) | CSNK2B-U | GST-CSNK2B<br>HA-CSNK2B | + (MEKK1ca)<br>+ (MEKK1ca) |
| ERK2 | MEK1 | Sanz-Moreno V (2003), Xu Be (2001), Chen Z (2001), Robinson F L (2002), Yeung K (2000), Wunderlich W (2001), Bardwell A J (2001) | MEK1-U,<br>U-MEK1 | GST-ERK2 | +<br>− |
| ERK2 | MEK2 | Robinson F L (2002), Bardwell A J (2001) | MEK2-U<br>U-MEK2 | GST-ERK2 | +<br>+ |
| JUN | FOS | Ito T (2001), Pognonec P (1997), Nomura N (1993), Venugopal R (1998), Yang X (1999), Finkel T (1993), Glover J N (1995), Vidal M (1996) Chevray P M (1992), Neznanov N (1997) | FOS-U<br>JUN-U | HA-JUN<br>GST-FOS | +<br>+ |
| JUN | JUN | Franklin C C (1995), Nomura N (1993), Yang X (1999), Chevray P M (1992), Zhang L (2005), Vidal M (1996) | JUN-U | HA-JUN | + |
| MK2 | p38α | Rane M J (2001), Janknecht R (2001), Engel K (1998), Ben-Levy R (1998) | U-MK2<br><br>MK2-U<br><br>U-p38α | GST-p38α<br>FLAG-p38α<br>GST-p38α<br>FLAG-p38α<br>Myc-MK2<br><br>GST-MK2<br><br>MK2-ST(377-393)<br>MK2-ST(377-391) | +<br>+<br>+<br>+<br>+<br>++ (MEKK1ca)<br>+<br>++ (MEKK1ca)<br>+<br>+ |
| MK2 | Edr2 | Yannoni Y M (2004) | U-MK2<br>MK2-U | GST-Edr2 | +<br>+ |
| MK2 | ERK2 | Yannoni Y M (2004) | U-MK2<br>ERK2-U | HA-ERK2<br>Myc-MK2 | +<br>(+) |
| MK5 | ERK3 | Schumacher S (2004), Seternes O M (2004), Déléris P (2008) | U-MK5 | GST-ERK3 | + |
| MK5 | p38α | New L (1998), Li Q (2008) | U-MK5 | FLAG-p38α | + |

TABLE 1A-continued

Protein-protein interactions verified by Trans-SUMOylation

| Protein 1 | Protein 2 | Reference | Protein1 fusions to Ubc9 | Protein2 constructs and mutants thereof | Trans-SUMOylation |
|---|---|---|---|---|---|
| | | | | GST-p38α | − |
| | | | U-p38α | HA-MK5 | + |
| PSMC3 | PSMC3 | Ishizuka T (2001) | U-PSMC3 | GST-PSMC3 | + |
| P38α | ERK2 | Sanz-Moreno V (2003), Tanoue T (2001) | ERK2-U | GST-p38α | − |
| | | | U-p38α | HA-ERK2 | + |
| | | | | GST-ERK2 | − |
| P38α | ERK1 | Sanz-Moreno V (2003) | U-p38α | ERK1 | + |
| p53 | CSNK2B | Schuster N (1999) | CSNK2B-U | p53 | + |
| | | | | p53K386R-ST(377-391) | + |
| | | | | p53K386R-ST(377-391) | + |
| | | | | p53K386R-ST(377-389) | + |
| | | | | p53K386R | − |
| | | | | p53K386R-3G-ST(377-393) | + |
| | | | | p53K386R-6G-ST(377-393) | + |
| | | | | p53K386R-ST(RAGP1) | − |
| | | | P53-U | GST-CSNK2B | − |
| | | | | | − (MEKK1ca) |
| p53 | p38α | Bulavin D V (1999) | U-p38α | p53 | + |
| | | | | p53K386R-ST(377-393) | + |
| | | | P53-U | Flag-p38α | − |
| | | | | GST-p38α | − |
| p53 | ERK2 | Persons D L (2000) | U-ERK2, | p53 | (+/−) |
| | | | | p53K386R-ST(377-393) | − |
| | | | ERK2-U | p53 | (+/−) |
| | | | | p53K386R-ST(377-393) | − |
| | | | P53-U | HA-ERK2 | + |

TABLE 1B

Protein-protein interactions not verified by Trans-SUMOylation

| Protein 1 | Protein 2 | Reference | Protein1 fusions to Ubc9 | Protein2 constructs | Trans-SUMOylation |
|---|---|---|---|---|---|
| CSNK2B | p38α | Sayed M (2000) | U-CSNK2B | GST-p38α | − |
| | | | | FLAG-p38α | − |
| | | | U-p38α | GST-CSNK2B | − (MEKK1) |
| JUN | JNK1 | Ishitani T (2003), Nishitoh H (1998), Derijard B (1994), Yazgan O (2002), Tada K (2001), Meyer C F (1996), Wiltshire C (2002), Choi B Y (2005), Janknecht R (1997), Li S (1997) | JUN-U | HA-JNK1 | − |
| JUN | JNK2 | Kallunki T (1996), Wiltshire C (2002), Fukunaga R (1997) | JUN-U | HA-JNK2 | − |
| MK2 | HSP27 | Rane M J (2001) McCormick C (2005) | U-MK2, MK2-U | HA-HSP27 | − |
| p38α | p38α | Kim M J (2003), Ge B (2002) | U-p38α | GST-p38α | − |
| p53 | TBP | Seto E (1992), Cvekl A (1999) | U-TBP | p53 | − |
| | | | | p53K386R-ST(377-393) | − |
| p53 | p53 | Sun X Z (2003) Rohaly G (2005), Weinberg R L (2004), Hanson S (2005) | p53-U | GST-p53 | (+/−) |
| p53 | JNK1 | Hu M C (1997), Fuchs S Y (1998) | p53-U | HA-JNK1 | − |
| p53 | JNK2 | Fuchs S Y (1998), Hu M C (1997) | p53-U | HA-JNK2 | − |
| p53 | ERK1 | Persons D L (2000) | p53-U | ERK1 | − |
| STAT1 | STAT1 | Li X (1996), Luker K E (2004), Mao X, 2005 | STAT1-U | STAT1-FKBP | − |

Protein-protein interactions described in the cited references were tested for Trans-SUMOylation. Each specific protein-protein interaction was tested by coexpression of different combinations of protein 1 fused to Ubc9 (U) with protein 2 mostly fused two a tag (HA, FLAG, Myc, GST, ST). (++), strong TransSUMOylation; (+), TransSUMOylation; (+/−) weak TransSUMOylation; (−) no detectable TransSUMOylation; (MEKK1ca) the activated MAP3 kinase MEKK1, that can enhance protein SUMOylation, was coexpressed.

TABLE 2A

New protein-protein interactions identified by Trans-SUMOylation

| Protein 1 | Protein 2 | Reference | Protein1 fusions to Ubc9 | Protein2 constructs | Trans-SUMOylation |
|---|---|---|---|---|---|
| CDC37 | CDC37 | — | U-CDC37 | GST-CDC37 | + |
| CSNK2B | MK2 | — | U-CSNK2B | GST-MK2 | (+/−) |
|  |  |  |  | Myc-MK2 | (+/−) |
|  |  |  |  | MK2-ST | − |
|  |  |  |  | MK2-ST(377-391) | − |
|  |  |  | MK2-U | GST-CSNK2B | + (MEKK1) |
|  |  |  | U-MK2 |  | − |
| HSF2BP | HSF2BP | — | U-HSF2BP | GST-HSF2BP | + (MEKK1) |
| MK2 | MK2 | — | U-MK2 | Myc-MK2 | + |
|  |  |  |  |  | − |
|  |  |  |  | GST-MK2 | + (MEKK1) |
|  |  |  |  |  | + |
|  |  |  |  |  | ++ (MEKK1) |
|  |  |  | MK2-U | Myc-MK2 | + |
|  |  |  |  |  | + (MEKK1) |
|  |  |  |  | GST-MK2 | + |
|  |  |  |  |  | ++ (MEKK1) |
| MK2 | ERK1 | — | U-MK2 | ERK1 | + |
| MK5 | MK2 | — | U-MK5 | GST-MK2 | (+/−) |
|  |  |  |  | Myc-MK2 | + |
|  |  |  |  | MK2-ST(377-393) | (+/−) |
|  |  |  |  | MK2-ST(377-391) | − |
|  |  |  | U-MK2 | HA-MK5 | − |
|  |  |  | MK2-U |  | − |
| p38α | Edr2 | — | U-p38α | GST-Edr2 | + |

TABLE 2B

No interaction detected with Trans-SUMOylation

| Protein 1 | Protein 2 | Reference | Protein1 fusions To Ubc9 | Protein2 constructs | Trans-SUMOylation |
|---|---|---|---|---|---|
| CDC37 | p38α | — | U-CDC37 | GST-p38α | − |
| CRSP9 | CRSP9 | — | CRSP9-U | GST-CRSP9 | − |
| ERK2 | ERK2 | — | ERK2-U | GST-ERK2 | − |
|  |  |  | U-ERK2 | GST-ERK2 | − |
| HSF2BP | HDGF | — | U-HDGF | GST-HSF2BP | − |
| JUN | CSNK2B | — | JUN | GST-CSNK2B | − |
| JUN | DRG1 | — | JUN-U | GST-DRG1 | − |
| JUN | ERK2 | — | JUN-U | HA-ERK2 | − |
| JUN | MK2 | — | MK2-U | HA-JUN | (+/−) |
|  |  |  | JUN-U | GST-MK2 | − |
|  |  |  |  | Myc-MK2 | − |
|  |  |  |  | MK2-ST(377-393) | − |
|  |  |  |  | MK2-ST(377-391) | − |
| JUN | p38α | — | JUN-U | FLAG-p38α | − |
|  |  |  |  | GST-p38α | − |
| MK2 | DRG1 | — | MK2-U | GST-DRG1 | − |
|  |  |  | U-MK2 |  | − |
| MK2 | FOS | — | MK2-U | GST-FOS | − |
| MK2 | JNK2 | — | U-MK2 | HA-JNK2 | − |
| MK2 | ERK3 | — | U-MK2 | GST-ERK3 | − |
| MK2 | TAF10 | — | MK2-U | GST-TAF10 | − |
| MK5 | CSNK2B | — | U-MK5 | GST-CSNK2B | − (MEKK1) |
|  |  |  | U-CSNK2B | HA-MK5 | − |
| MK5 | DRG1 | — | U-MK5 | GST-DRG1 | − |
| MK5 | MK5 | — | U-MK5 | HA-MK5 | (+/−) |
| MK5 | JUN | — | JUN-U | HA-MK5 | − |
| MK5 | JNK2 | — | U-MK5 | HA-JNK2 | − |
| MK5 | ERK2 | — | U-ERK2, ERK2-U | HA-MK5 | (+/−) |
|  |  |  | U-MK5 | GST-ERK2 | − |
| PSMC3 | MK2 | — | MK2-U | GST-PSMC3 | − |
| p38α | DRG1 | — | U-p38α | GST-DRG1 | − |
| p38α | JNK2 | — | U-p38α | HA-JNK2 | − |
| p38α | ERK3 | — | U-p38α | GST-ERK3 | − |
| P53 | DRG1 | — | p53-U | GST-DRG1 | − |
| P53 | MK2 | — | U-MK2 | p53 | − |
|  |  |  | MK2-U |  | − |
|  |  |  | U-MK2 | p53K386R-ST(377-393) | − |
|  |  |  |  | p53K386R-ST(377-391) | − |
|  |  |  |  | p53K386R-ST(377-389) | − |
|  |  |  | p53-U | Myc-MK2 | − |
|  |  |  |  | GST-MK2 | − |

TABLE 2B-continued

| | | | Protein1 fusions | Protein2 | Trans- |
|---|---|---|---|---|---|
| Protein 1 | Protein 2 | Reference | To Ubc9 | constructs | SUMOylation |

| | | | | | |
|---|---|---|---|---|---|
| | | | | MK2-ST(377-393) | – |
| | | | | MK2-ST(377-391) | – |
| P53 | Edr2 | — | p53-U | GST-Edr2 | – |
| P53 | CDK4 | — | U-CDK4 | p53 | – |
| | | | | p53K386R-ST(377-393) | – |
| | | | p53-U | GST-CDK4 | – |
| P53 | STAT1 | — | STAT1-U | p53 | – |
| | | | | p53K386R-ST(377-393) | – |
| STAT1 | MK2 | — | MK2-U | STAT1-FKBP | – |
| TAF10 | TAF10 | — | U-TAF10 | GST-TAF10 | (+/–) |

Protein-protein interaction of each pair of protein 1/protein 2 was tested by coexpression of different combinations of a protein 1 fused to Ubc9 (U) with protein 2 mostly fused two a Tag (HA, FLAG, GST, ST). (++), strong TransSUMOylation; (+), TransSUMOylation; (+/–) weak TransSUMOylation; (–) no detectable TransSUMOylation; (MEKK1ca), the activated MAP3 kinase MEKK1, that can enhance protein SUMOylation, was coexpressed.

REFERENCES IN THE TABLE

Stepanova, L., Leng, X., Parker, S. B. and Harper, J. W. (1996) Mammalian p50Cdc37 is a protein kinase-targeting subunit of Hsp90 that binds and stabilizes Cdk4. *Genes Dev.*, 10, 1491-1502.

Ewing, R. M., Chu, P., Elisma, F., Li, H., Taylor, P., Climie, S., McBroom-Cerajewski, L., Robinson, M. D., O'Connor, L., Li, M., et al. (2007) Large-scale mapping of human protein-protein interactions by mass spectrometry. *Mol. Syst. Biol.*, 3, 89.

Dai, K., Kobayashi, R. and Beach, D. (1996) Physical interaction of mammalian CDC37 with CDK4. *J. Biol. Chem.*, 271, 22030-22034.

Lamphere, L., Fiore, F., Xu, X., Brizuela, L., Keezer, S., Sardet, C., Draetta, G. F. and Gyuris, J. (1997) Interaction between Cdc37 and Cdk4 in human cells. *Oncogene*, 14, 1999-2004.

Lehner, B., Semple, J. I., Brown, S. E., Counsell, D., Campbell, R. D. and Sanderson, C. M. (2004) Analysis of a high-throughput yeast two-hybrid system and its use to predict the function of intracellular proteins encoded within the human MHC class III region. *Genomics*, 83, 153-167.

Kim, M. S., Lee, Y. T., Kim, J. M., Cha, J. Y. and Bae, Y. S. (1998) Characterization of protein interaction among subunits of protein kinase CKII in vivo and in vitro. *Mol. Cells.*, 8, 43-48.

Marin, O., Meggio, F., Sarno, S. and Pinna, L. A. (1997) Physical dissection of the structural elements responsible for regulatory properties and intersubunit interactions of protein kinase CK2 beta-subunit. *Biochemistry*, 36, 7192-7198.

Niefind, K., Guerra, B., Ermakowa, I. and Issinger, O. G. (2001) Crystal structure of human protein kinase CK2: insights into basic properties of the CK2 holoenzyme. *EMBO J.*, 20, 5320-5331.

Niefind, K., Guerra, B., Ermakowa, I. and Issinger, O. G. (2000) Crystallization and preliminary characterization of crystals of human protein kinase CK2. *Acta Crystallogr. D. Biol. Crystallogr.*, 56, 1680-1684.

Gietz, R. D., Graham, K. C. and Litchfield, D. W. (1995) Interactions between the subunits of casein kinase II. *J. Biol. Chem.*, 270, 13017-13021.

Sanz-Moreno, V., Casar, B. and Crespo, P. (2003) p38alpha isoform Mxi2 binds to extracellular signal-regulated kinase 1 and 2 mitogen-activated protein kinase and regulates its nuclear activity by sustaining its phosphorylation levels. *Mol. Cell. Biol.*, 23, 3079-3090.

Xu, Be., Stippec, S., Robinson, F. L. and Cobb, M. H. (2001) Hydrophobic as well as charged residues in both MEK1 and ERK2 are important for their proper docking. *J. Biol. Chem.*, 276, 26509-26515.

Chen, Z. and Cobb, M. H. (2001) Regulation of stress-responsive mitogen-activated protein (MAP) kinase pathways by TA02. *J. Biol. Chem.*, 276, 16070-16075.

Robinson, F. L., Whitehurst, A. W., Raman, M. and Cobb, M. H. (2002) Identification of novel point mutations in ERK2 that selectively disrupt binding to MEK1. *J. Biol. Chem.*, 277, 14844-14852.

Yeung, K., Janosch, P., McFerran, B., Rose, D. W., Mischak, H., Sedivy, J. M., Kolch, W. (2000) Mechanism of suppression of the Raf/MEK/extracellular signal-regulated kinase pathway by the raf kinase inhibitor protein. *Mol. Cell. Biol.*, 20, 3079-3085.

Wunderlich, W., Fialka, I., Teis, D., Alpi, A., Pfeifer, A., Parton, R. G., Lottspeich, F. (2001) Huber L A. A novel 14-kilodalton protein interacts with the mitogen-activated protein kinase scaffold mp1 on a late endosomal/lysosomal compartment. *J. Cell. Biol.*, 152, 765-776.

Bardwell, A. J., Flatauer, L. J., Matsukuma, K., Thorner, J. and Bardwell, L. (2001) A conserved docking site in MEKs mediates high-affinity binding to MAP kinases and cooperates with a scaffold protein to enhance signal transmission. *J. Biol. Chem.*, 276, 10374-10386.

Ito, T., Yamauchi, M., Nishina, M., Yamamichi, N., Mizutani, T., Ui, M., Murakami, M. and Iba, H. (2001) Identification of SWI.SNF complex subunit BAF60a as a determinant of the transactivation potential of Fos/Jun dimers. *J. Biol. Chem.*, 276, 2852-2857.

Pognonec, P., Boulukos, K. E., Aperlo, C., Fujimoto, M., Ariga, H., Nomoto, A. and Kato, H. (1997) Cross-family interaction between the bHLHZip USF and bZip Fra1 proteins results in down-regulation of AP1 activity. *Oncogene*, 14, 2091-2098.

Nomura, N., Zu, Y. L., Maekawa, T., Tabata, S., Akiyama, T. and Ishii, S. (1993) Isolation and characterization of a novel member of the gene family encoding the cAMP response element-binding protein CRE-BP1. *J. Biol. Chem.*, 268, 4259-4266.

Venugopal, R. and Jaiswal, A. K. (1998) Nrf2 and Nrf1 in association with Jun proteins regulate antioxidant response element-mediated expression and coordinated induction of genes encoding detoxifying enzymes. *Oncogene*, 17, 3145-3156.

Yang, X., Chen, Y. and Gabuzda, D. (1999) ERK MAP kinase links cytokine signals to activation of latent HIV-1 infection by stimulating a cooperative interaction of AP-1 and NF-kappaB. *J. Biol. Chem.*, 274, 27981-27988.

Finkel, T., Duc, J., Fearon, E. R., Dang, C. V. and Tomaselli, G. F. (1993) Detection and modulation in vivo of helix-loop-helix protein-protein interactions. *J. Biol. Chem.*, 268, 5-8.

Glover, J. N. and Harrison, S. C. (1995) Crystal structure of the heterodimeric bZIP transcription factor c-Fos-c-Jun bound to DNA. *Nature*, 373, 257-261.

Vidal, M., Brachmann, R. K., Fattaey, A., Harlow, E. and Boeke, J. D. (1996) Reverse two-hybrid and one-hybrid systems to detect dissociation of protein-protein and DNA-protein interactions. *Proc. Natl. Acad. Sci. U S A*, 93, 10315-10320.

Chevray, P. M. and Nathans, D. (1992) Protein interaction cloning in yeast: identification of mammalian proteins that react with the leucine zipper of Jun. *Proc. Natl. Acad. Sci. U S A*, 89, 5789-5793.

Neznanov, N., Umezawa, A. and Oshima, R. G. (1997) A regulatory element within a coding exon modulates keratin 18 gene expression in transgenic mice. *J. Biol. Chem.*, 272, 27549-27557.

Franklin, C. C., McCulloch, A. V. and Kraft, A. S. (1995) In vitro association between the Jun protein family and the general transcription factors, TBP and TFIIB. *Biochem. J.*, 305, 967-974.

Zhang, L., Xing, G., Tie, Y., Tang, Y., Tian, C., Li, L., Sun, L., Wei, H., Zhu, Y. and He, F. (2005) Role for the pleckstrin homology domain-containing protein CKIP-1 in AP-1 regulation and apoptosis. *EMBO J.*, 24, 766-778.

Rane, M. J., Coxon, P. Y., Powell, D. W., Webster, R., Klein, J. B., Pierce, W., Ping, P. and McLeish, K. R. (2001) p38 Kinase-dependent MAPKAPK-2 activation functions as 3-phosphoinositide-dependent kinase-2 for Akt in human neutrophils. *J. Biol. Chem.*, 276, 3517-3523.

Janknecht, R. and Hunter, T. (1997) Activation of the Sap-1a transcription factor by the c-Jun N-terminal kinase (JNK) mitogen-activated protein kinase. *J. Biol. Chem.*, 272, 4219-4224.

Engel, K. Kotlyarov, A. and Gaestel, M. (1998) Leptomycin B-sensitive nuclear export of MAPKAP kinase 2 is regulated by phosphorylation. *EMBO J.*, 17, 3363-3371.

Ben-Levy, R., Hooper, S., Wilson, R., Paterson, H. F. and Marshall, C. J. (1998) Nuclear export of the stress-activated protein kinase p38 mediated by its substrate MAP-KAP kinase-2. *Curr. Biol.*, 8, 1049-1057.

Yannoni, Y. M., Gaestel M. and Lin, L. L. (2004) P66(ShcA) interacts with MAPKAP kinase 2 and regulates its activity. *FEBS Lett.*, 564, 205-211.

Schumacher, S., Laass, K., Kant, S., Shi, Y., Visel, A., Gruber, A. D., Kotlyarov, A., and Gaestel, M. (2004)Scaffolding by ERK3 regulates MK5 in development. *EMBO J.*, 23, 4770-4779.

Seternes, O. M., Mikalsen, T., Johansen, B., Michaelsen, E., Armstrong, C. G., Morrice, N. A., Turgeon, B., Meloche, S., Moens, U. and Keyse, S. M. (2005) Activation of MK5/PRAK by the atypical MAP kinase ERK3 defines a novel signal transduction pathway. *EMBO J.*, 23, 4780-91 2004. Erratum in: *EMBO J.* 24, 873.

Déléris, P., Rousseau, J., Coulombe, P., Rodier, G., Tanguay, P. L. and Meloche, S. (2008) Activation loop phosphorylation of the atypical MAP kinases ERK3 and ERK4 is required for binding, activation and cytoplasmic relocalization of MK5. *J. Cell. Physiol.*, 217, 778-788.

New, L., Jiang, Y., Zhao, M., Liu, K., Zhu, W., Flood, L. J., Kato, Y., Parry, G. C. and Han, J. (1998 PRAK, a novel protein kinase regulated by the p38 MAP kinase. *EMBO J.*, 17, 3372-3384.

Li, Q., Zhang, N., Zhang, D., Wang, Y., Lin, T., Wang, Y., Zhou, H., Ye, Z., Zhang, F., Lin, S. C. and Han, J. (2008) Determinants that control the distinct subcellular localization of p38alpha-PRAK and p38beta-PRAK complexes. *J. Biol. Chem.*, 283, 11014-11023.

Ishizuka, T., Satoh, T., Monden, T., Shibusawa, N., Hashida, T., Yamada, M. and Mori, M. (2001) Human immunodeficiency virus type 1 Tat binding protein-1 is a transcriptional coactivator specific for TR. *Mol. Endocrinol.*, 15, 1329-1343.

Tanoue, T., Maeda, R., Adachi, M. and Nishida, E. (2001) Identification of a docking groove on ERK and p38 MAP kinases that regulates the specificity of docking interactions. *EMBO J.*, 20, 466-479.

Schuster, N., Prowald, A., Schneider, E., Scheidtmann, K. H. and Montenarh, M. (1999) Regulation of p53 mediated transactivation by the beta-subunit of protein kinase CK2. *FEBS Lett.*, 447, 160-166.

Bulavin, D. V., Saito, S., Hollander, M. C., Sakaguchi, K., Anderson, C. W., Appella, E. and Fornace, A. J., Jr. (1999) Phosphorylation of human p53 by p38 kinase coordinates N-terminal phosphorylation and apoptosis in response to UV radiation. *EMBO J.*, 18, 6845-6854. revisited Persons, D. L., Yazlovitskaya, E. M. and Pelling, J. C. (2000) Effect of extracellular signal-regulated kinase on p53 accumulation in response to cisplatin. *J. Biol. Chem.*, 275, 35778-35785.

Sayed, M., Kim, S. O., Salh, B. S., Issinger, O. G. and Pelech, S. L. (2000) Stress-induced activation of protein kinase CK2 by direct interaction with p38 mitogen-activated protein kinase. *J. Biol. Chem.*, 275, 16569-16573.

Ishitani, T., Takaesu, G., Ninomiya-Tsuji, J., Shibuya, H., Gaynor, R. B. and Matsumoto, K. (2003) Role of the TAB2-related protein TAB3 in IL-1 and TNF signaling. *EMBO J.*, 22, 6277-6288.

Nishitoh, H., Saitoh, M., Mochida, Y., Takeda, K., Nakano, H., Rothe, M., Miyazono, K. and Ichijo, H. (1998) ASK1 is essential for JNK/SAPK activation by TRAF2. *Mol. Cell*, 2, 389-395.

Dérijard, B., Hibi, M., Wu, I. H., Barrett, T., Su, B., Deng, T., Karin, M. and Davis, R. J. (1994) JNK1: a protein kinase stimulated by UV light and Ha-Ras that binds and phosphorylates the c-Jun activation domain. *Cell*, 76, 1025-1037.

Yazgan, O. and Pfarr, C. M. (2002) Regulation of two JunD isoforms by Jun N-terminal kinases. *J. Biol. Chem.*, 277, 29710-29718.

Tada, K., Okazaki, T., Sakon, S., Kobarai, T., Kurosawa, K., Yamaoka, S., Hashimoto, H., Mak, T. W., Yagita, H., Okumura, K., Yeh, W. C. and Nakano, H. (2001) Critical roles of TRAF2 and TRAF5 in tumor necrosis factor-induced NF-kappa B activation and protection from cell death. *J. Biol. Chem.*, 276, 36530-36534.

Meyer, C. F., Wang, X., Chang, C., Templeton, D. and Tan, T. H. (1996) Interaction between c-Rel and the mitogen-activated protein kinase kinase kinase 1 signaling cascade in mediating kappaB enhancer activation. *J. Biol. Chem.*, 271, 8971-8976.

Wiltshire, C., Matsushita, M., Tsukada, S., Gillespie, D. A. and May, G. H. (2002) A new c-Jun N-terminal kinase (JNK)-interacting protein, Sab (SH3BP5), associates with mitochondria. *Biochem. J.*, 367, 577-585.

Choi, B. Y., Choi, H. S., Ko, K., Cho, Y. Y., Zhu, F., Kang, B. S., Ermakova, S. P., Ma, W. Y., Bode, A. M. and Dong, Z. (2005) The tumor suppressor p16(INK4a) prevents cell transformation through inhibition of c-Jun phosphorylation and AP-1 activity. *Nat. Struct. Mol. Biol.*, 12, 699-707.

Li, S., Kim, M., Hu, Y. L., Jalali, S., Schlaepfer, D. D., Hunter, T., Chien, S., Shyy, J. Y. (1997) Fluid shear stress activation of focal adhesion kinase. Linking to mitogen-activated protein kinases. *J. Biol. Chem.*, 272, 30455-30462.

Kallunki, T., Deng, T., Hibi, M. and Karin, M. (1996) c-Jun can recruit JNK to phosphorylate dimerization partners via specific docking interactions. *Cell*, 87, 929-939.

Fukunaga, R. and Hunter, T. (1997) MNK1, a new MAP kinase-activated protein kinase, isolated by a novel expression screening method for identifying protein kinase substrates. *EMBO J.*, 16, 1921-1933.

McCormick, C. and Ganem, D. (2005) The kaposin B protein of KSHV activates the p38/MK2 pathway and stabilizes cytokine mRNAs. *Science*, 307, 739-741.

Kim, M. J., Park, B. J., Kang, Y. S., Kim, H. J., Park, J. H., Kang, J. W., Lee, S. W., Han, J. M., Lee, H. W. and Kim, S. (2003) Downregulation of FUSE-binding protein and c-myc by tRNA synthetase cofactor p38 is required for lung cell differentiation. *Nat. Genet.*, 34, 330-336.

Ge, B., Gram, H., Di Padova, F., Huang, B., New, L., Ulevitch, R. J., Luo, Y. and Han, J. (2002) MAPKK-independent activation of p38alpha mediated by TAB1-dependent autophosphorylation of p38alpha. *Science*, 295, 1291-1294.

Seto, E., Usheva, A., Zambetti, G. P., Momand, J., Horikoshi, N., Weinmann, R., Levine, A. J. and Shenk, T. (1992) Wild-type p53 binds to the TATA-binding protein and represses transcription. *Proc. Natl. Acad. Sci. U S A*, 89, 12028-12032.

Cvekl, A., Kashanchi, F., Brady, J. N. and Piatigorsky, J. (1999) Pax-6 interactions with TATA-box-binding protein and retinoblastoma protein. *Invest. Ophthalmol. Vis. Sci.*, 40, 1343-1350.

Sun, X. Z., Vinci, C., Makmura, L., Han, S., Tran, D., Nguyen, J., Hamann, M., Grazziani, S., Sheppard, S., Gutova, M., Zhou, F., Thomas, J. and Momand, J. (2003). Formation of disulfide bond in p53 correlates with inhibition of DNA binding and tetramerization. *Antioxid. Redox. Signal.*, 5, 655-665.

Rohaly, G., Chemnitz, J., Dehde, S., Nunez, A. M., Heukeshoven, J., Deppert, W. and Dornreiter, I. (2005) A novel human p53 isoform is an essential element of the ATR-intra-S phase checkpoint. *Cell*, 122, 21-32.

Weinberg, R. L., Veprintsev, D. B. and Fersht, A. R. (2004) Cooperative binding of tetrameric p53 to DNA. *J. Mol. Biol.*, 341, 1145-1159.

Hanson, S., Kim, E. and Deppert, W. (2005) Redox factor 1 (Ref-1) enhances specific DNA binding of p53 by promoting p53 tetramerization. *Oncogene*, 24, 1641-1647.

Hu, M. C., Qiu, W. R. and Wang, Y. P. (1997) JNK1, JNK2 and JNK3 are p53 N-terminal serine 34 kinases. *Oncogene*, 15, 2277-2287.

Fuchs, S. Y., Adler, V., Buschmann, T., Yin, Z., Wu, X., Jones, S. N. and Ronai, Z. (1998) JNK targets p53 ubiquitination and degradation in nonstressed cells. *Genes Dev.*, 12, 2658-2663.

Li, X., Leung, S., Qureshi, S., Darnell, J. E., Jr. and Stark, G. R. (1996) Formation of STAT1-STAT2 heterodimers and their role in the activation of IRF-1 gene transcription by interferon-alpha. *J. Biol. Chem.*, 271, 5790-5794.

Luker, K. E., Smith, M. C., Luker, G. D., Gammon, S. T., Piwnica-Worms, H., and Piwnica-Worms, D. (2004) Kinetics of regulated protein-protein interactions revealed with firefly luciferase complementation imaging in cells and living animals. *Proc. Natl. Acad. Sci. U S A*, 101, 12288-12293.

Mao, X., Ren, Z., Parker, G. N., Sondermann, H., Pastorello, M. A., Wang, W., McMurray, J. S., Demeler, B., Darnell, J. E., Jr. and Chen, X. (2005) Structural bases of unphosphorylated STAT1 association and receptor binding. *Mol. Cell*, 17, 761-77.

The invention claimed is:

1. A method for determining SUMOylation of a molecule of interest comprising the steps of
   a) providing a first construct comprising Ubc9 or a homologue thereof having Ubc9 enzymatic activity and fused therewith a first moiety of a binding pair allowing for specific binding with the second moiety of said binding pair;
   b) providing the molecule of interest fused with said second moiety of the binding pair which specifically interacts with the first moiety of a binding pair fused with Ubc9 or a homologue thereof having Ubc9 enzymatic activity;
   c) optionally providing SUMO molecules being marked with a marker molecule;
   d) allowing binding of said first moiety of a binding pair with said second moiety of said binding pair;
   e) optionally, inducing binding between the two moieties of the binding pair in step d) by providing a molecule inducing formation of a complex of the first moiety of said binding pair and the second moiety of said binding pair;
   f) determining conjugation of SUMO molecule(s) with the molecule of interest fused with the second moiety of said binding pair.

2. A method for screening and, optionally, identifying specific interaction between a first predetermined binding molecule and a binding partner thereof comprising the step of
   a) providing a first construct comprising Ubc9 or a homologue thereof having Ubc9 enzymatic activity fused to the first predetermined binding molecule for which specific binding molecules should be detected;
   b) optionally providing SUMO molecules being marked with a marker molecule;
   c) allowing interaction between the binding molecule of the first construct with potential specific binding partners of said first binding molecule in an environment allowing binding of said binding partners and allowing SUMOylation of the binding partner after specific interaction between the first binding molecule and the binding partner; and
   d) detecting SUMOylation of potential specific binding painters of the first binding molecule fused with Ubc9 or a homologue thereof having Ubc9 enzymatic activity.

3. The method according to claim 2 wherein the potential binding partners of the first binding molecule fused with Ubc9 or a homologue thereof having Ubc9 enzymatic activity allowing for specific interaction with the first binding molecule comprise a domain comprising a SUMOylation site.

4. The method according to claim 1 which is conducted in a cell-free system.

5. The method according to claim 1 using a transfected cell line containing a construct comprising Ubc9 or a homologue thereof having Ubc9 enzymatic activity fused with the first binding molecule or the first moiety of a binding pair.

6. The method according to claim 1 wherein the binding pair is FKBP and FKBP derivatives and FRB and FRB derivatives allowing formation of a binding complex.

7. The method according to claim 6, wherein the binding of the binding pair FKBP and FRB is induced by providing rapamycin and rapamycin derivatives.

8. The method according to claim 1, wherein the molecule of interest or the potential binding partners are modified with a domain to comprise a SUMOylation site.

9. The method according to claim 1 wherein the molecule of interest or the potential binding partners are modified with a tag allowing purification of the molecule of interest or the potential binding partners.

10. The method according to claim 9 wherein the tag allowing purification is selected from the group of a STREP-group, a GST-group, a bioease-group or protein-A-tag.

11. The method according to claim 1, wherein SUMO molecules are provided exogenously and said SUMO molecules contain i) a marker moiety, in particular, said SUMO molecules are linked with a luciferase molecule, and/or ii) a moiety allowing purification of the SUMO molecules.

12. The method according to claim 1, wherein SUMO molecules are provided exogenously and said SUMO molecules contain a domain comprising a SUMOylation site.

13. A vector comprising a nucleic acid molecule encoding a peptide having Ubc9 enzymatic activity and fused to a nucleic acid molecule encoding a second peptide, said second peptide represents the first binding molecule which enable specific binding with a binding partner which may be SUMOylated due to interaction with the first binding molecule whereby binding is induced by providing a binding inducing molecule exogenously.

14. The vector according to claim 13 wherein the first binding molecule is the FRB domain or derivatives thereof enabling binding with the FKBP domain or derivatives thereof as part of the binding partner and the molecule inducing heterodimer formation is rapamycin or derivatives thereof.

15. A system for determining SUMOylation of a molecule of interest comprising a first construct comprising Ubc9 or a homologue thereof having Ubc9 enzymatic activity and fused therewith a first moiety of a binding pair allowing for specific binding with the second moiety of said binding pair, a second construct allowing fusion and expression of a molecule of interest with said second moiety of said binding pair, and, optionally, means for the determination of SUMOylation.

16. A system for detection of SUMOylation of a potential specific binding pal titer of a first predetermined binding molecule comprising a first construct comprising Ubc9 or a homologue thereof having Ubc9 enzymatic activity and means for introducing the first predetermined binding molecule into said construct to obtain Ubc9 or a homologue thereof having Ubc9 enzymatic activity fused and operably linked with said predetermined binding molecule, SUMO molecules containing a marker moiety, and, optionally, means for detection of SUMOylation of potential specific binding partners of the first predetermined binding molecule.

17. The system according to claim 16 further comprising means for preparing and expressing potential specific binding partners of a predetermined binding molecule having a domain containing a SUMOylation site.

18. The system according to claim 15 further comprising a heterodimer formation inducing molecule interaction specifically with the first binding moiety and the second binding moiety, in particular, the heterodimer formation inducible molecule is rapamycin and derivatives thereof.

19. The system according to claim 15 comprising a cell line containing at least the construct of Ubc9 or a homologue thereof having Ubc9 enzymatic activity fused and operably linked with the first binding molecule.

* * * * *